(12) United States Patent
Wang et al.

(10) Patent No.: US 11,594,323 B2
(45) Date of Patent: Feb. 28, 2023

(54) HEALTH CARE FACILITY UNIT COMPUTER SIMULATION SYSTEM

(71) Applicant: KONINKLIJKE PHILIPS N.V., Eindhoven (NL)

(72) Inventors: Wei Wang, Somerville, MA (US); Yugang Jia, Winchester, MA (US); Reza Sharifi Sedeh, Malden, MA (US); Yang Yang, Medford, MA (US)

(73) Assignee: Koninklijke Philips N.V., Eindhoven (NL)

( * ) Notice: Subject to any disclaimer, the term of this patent is extended or adjusted under 35 U.S.C. 154(b) by 190 days.

(21) Appl. No.: 16/319,497

(22) PCT Filed: Jul. 31, 2017

(86) PCT No.: PCT/EP2017/069310
§ 371 (c)(1),
(2) Date: Jan. 22, 2019

(87) PCT Pub. No.: WO2018/024672
PCT Pub. Date: Feb. 8, 2018

(65) Prior Publication Data
US 2021/0287781 A1    Sep. 16, 2021

Related U.S. Application Data

(60) Provisional application No. 62/369,794, filed on Aug. 2, 2016.

(51) Int. Cl.
*G16H 40/20* (2018.01)
*G16H 50/70* (2018.01)

(52) U.S. Cl.
CPC ............. *G16H 40/20* (2018.01); *G16H 50/70* (2018.01)

(58) Field of Classification Search
CPC .............................. G16H 40/20; G16H 50/70
See application file for complete search history.

(56) References Cited

U.S. PATENT DOCUMENTS

| 7,925,603 B1 | 4/2011 | Laidig et al. |
| 9,311,449 B2 | 4/2016 | Levin et al. |

(Continued)

FOREIGN PATENT DOCUMENTS

WO    2000077665 A2    12/2000

OTHER PUBLICATIONS

Vilar et al., Non-linear time series clustering based on non-parametric forecast densities, 54 Computational Statistics and Data Analysis 2850-2865 (Year: 2010).*

(Continued)

*Primary Examiner* — Evangeline Barr
*Assistant Examiner* — Jordan L Jackson

(57) ABSTRACT

The present disclosure pertains to a system configured to generate computer simulations of patient loads for units of health care facilities. The system is configured to: obtain past patient census information for an individual unit of a health care facility, the past patient census information comprising a quantity of patient visits to the individual unit during past periods of time; determine intra-period variation and inter-period variation in the quantity of patient visits to the individual unit during the past periods of time; classify the individual unit based on the intra-period and inter-period variations; and generate a computer simulation of patient loads for the individual unit based on the classification. The computer-simulated patient loads comprise a quantity of patient visits to the individual unit during one or more future periods of time. The computer simulation is performed using a non-parametric simulation algorithm.

15 Claims, 6 Drawing Sheets

(56) References Cited

U.S. PATENT DOCUMENTS

2004/0019504  A1      1/2004  Korom et al.
2010/0198609  A1 *    8/2010  Mellin .................. G06Q 10/00
                                                      705/2
2014/0108034  A1 *    4/2014  Akbay ............. G06Q 10/06315
                                                      705/2

OTHER PUBLICATIONS

Vermeulen, I. et al., "Adaptive resource allocation for efficient patient scheduling", Artificial Intelligence in Medicine, 2009.
Burke, E. et al., "The State of the Art of Nursing Rostering", Journal of Scheduling, 2004.
Zeltyn, S. et al., "Simulation-Based Models of Emergency Departments: Operational, Tactical and Strategic Staffing", Rambam Health Care Center, Israel, 2011.
Zuidhof, G., "Capacity Planning of Ambulance Services: Statistical Analysis, Forecasting and Staffing", University of Amsterdam, Jul. 2012.

\* cited by examiner

HEALTH CARE FACILITY UNIT COMPUTER SIMULATION SYSTEM

CROSS-REFERENCE TO PRIOR APPLICATIONS

This application is the U.S. National Phase application under 35 U.S.C. § 371 of International Application No. PCT/EP2017/069310, filed on 31 Jul. 2017, which claims the benefit of U.S. Provisional Patent Application No. 62/369,794, filed on 2 Aug. 2016. These applications are hereby incorporated by reference herein.

BACKGROUND

1. Field

The present disclosure pertains to a system configured to generate computer simulations of patient loads for units of health care facilities.

2. Description of the Related Art

Staff scheduling is a well-known problem within units of health care facilities. Different units, by nature, have different patient visit patterns. For example, emergency departments have consistent daily fluctuations. At in-patient units, patient visit numbers tend to stay constant overall but exhibit random fluctuations in admissions and/or discharges often within a single day. Patient visit numbers are typically stochastic in nature. Even for the most stable units, the patient visit numbers for one week may not match the patient visit numbers for another week.

Staffing level recommendation systems for health care facilities are known. Maintaining an optimal staffing level and a reasonable caregiver shift table, while also maintaining clinically sound caregiver coverage and respecting idiosyncratic regulations and constraints is a challenging task for health care facilities. The typical health care facility unit-to-unit non-heterogeneity and stochastic nature of patient census numbers create a hurdle for traditional schedule-optimization tools that usually have a specific deterministic target. Typical raw historical census data is often noisy and requires modelling and adjustment to determine useful information. Evaluating the statistical properties of the historical census data typically requires more data than is realistically available. Traditional parametric simulation algorithms are rigid and artificially reduce corresponding uncertainties in patient visit fluctuation numbers.

SUMMARY

Accordingly, one or more aspects of the present disclosure relate to a system configured to generate computer simulations of patient loads for units of health care facilities. The system comprises one or more hardware processors and/or other components. The one or more hardware processors are configured by machine readable instructions to: obtain past patient census information for an individual unit of a health care facility, the past patient census information comprising a quantity of patient visits to the individual unit during past periods of time; determine intra-period variation and inter-period variation in the quantity of patient visits to the individual unit during the past periods of time; classify the individual unit based on the intra-period and inter-period variations; and generate a computer simulation of patient loads for the individual unit based on the classification. The computer-simulated patient loads comprise a quantity of patient visits to the individual unit during one or more future periods of time. The computer simulation is performed using a non-parametric simulation algorithm. In some embodiments, the quantities of patient visits (e.g., past and future) may be and/or include a quantity of patients visiting (e.g., admitted by the unit, being treated by the unit, housed within the unit, etc.) the individual unit at a given time.

Yet another aspect of the present disclosure relates to a method for generating computer simulations of patient loads for units of health care facilities with a simulation system. The system comprises one or more hardware processors configured by machine readable instructions and/or other components. The method comprises: obtaining past patient census information for an individual unit of a health care facility, the past patient census information comprising a quantity of patient visits to the individual unit during past periods of time; determining intra-period variation and inter-period variation in the quantity of patient visits to the individual unit during the past periods of time; classifying the individual unit based on the intra-period and inter-period variations; and generating a computer simulation of patient loads for the individual unit based on the classification. The computer-simulated patient loads comprise a quantity of patient visits to the individual unit during one or more future periods of time. The computer simulation is performed using a non-parametric simulation algorithm.

Still another aspect of the present disclosure relates to a system for generating computer simulations of patient loads for units of health care facilities. The system comprises: means for obtaining past patient census information for an individual unit of a health care facility, the past patient census information comprising a quantity of patient visits to the individual unit during past periods of time; means for determining intra-period variation and inter-period variation in the quantity of patient visits to the individual unit during the past periods of time; means for classifying the individual unit based on the intra-period and inter-period variations; and means for generating a computer simulation of patient loads for the individual unit based on the classification. The computer-simulated patient loads comprise a quantity of patient visits to the individual unit during one or more future periods of time. The computer simulation is performed using a non-parametric simulation algorithm.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
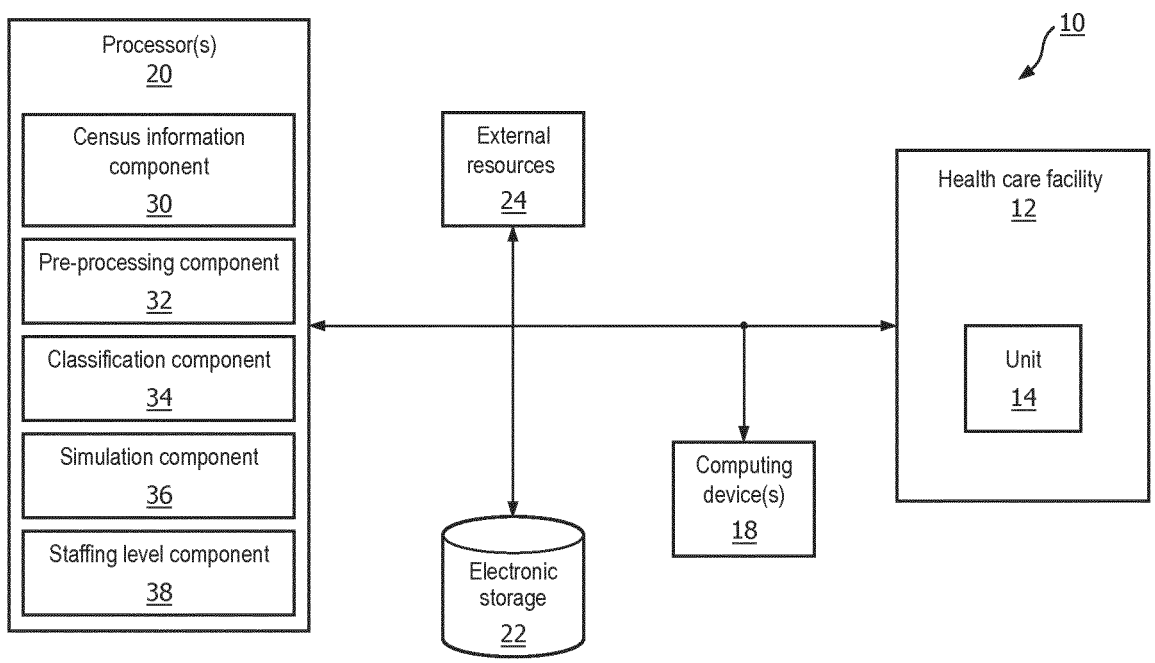
FIG. 1 is a schematic illustration of a system configured to generate computer simulations of patient loads for units of health care facilities, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to generate computer simulations of patient loads for units 14 of health care facilities 12, in accordance with one or more embodiments. System 10 is configured to classify individual units 14 of health care facilities 12 based on historical patient census information (e.g., a number of patient visits to an individual unit 14 over previous periods of time) and use tailored simulation algorithms for individual units 14 based on the classification to generate the computer simulations of patient loads. The computer simulations of patient loads may be used to optimize staffing levels for and individual unit 14. In some embodiments, the quantities of patient visits (e.g., past, future, etc.) and/or patient loads described herein may be and/or include a quantity of patients visiting (e.g., admitted by the unit, being treated by the unit, housed within the unit, etc.) an individual unit 14 at a given time (e.g., a count of a total quantity of patients in a unit at given time).

System 10 is configured to classify units 14 based on weekly (and/or other time periods such as hourly, daily, monthly, yearly, etc.) patient census information. System 10 is configured to classify units 14 based on inter-period (e.g., inter-week or other inter-period) variations and/or intra-period (e.g., intra-week or other intra-period) variation. System 10 is configured to classify individual units 14 into at least one patient visit pattern category. As an example, categories (or a category) in which an individual unit 14 may be classified include a predictable-variable patient census information pattern where there are high intra-period (e.g., intra-week or other intra-period) variations and/or low inter-period variations in the number of patients that visit a given unit 14; a mixed-variable pattern where there are both high intra-period variations and inter-period variations, a shifting-flat pattern where there are high inter-period variations and low intra-period variations, a stable-flat pattern that is low in both inter-period and intra-period variations, and/or other categories. System 10 is configured to use targeted non-parametric simulation algorithms for different units 14 with different patient census profiles (e.g., categorized in different patient visit pattern categories) to simulate patient loads (e.g., future patient loads) on the individual units.

Advantageously, system 10 provides individualized computer-simulated patient loads for units 14 with non-heterogeneous geographic locations, clinical specialties, and/or other characteristics. System 10 is configured to gather historical patient census information, generate computer-simulated patient loads for individual units 14 based on the historical census information, optimize a staffing level for a unit 14 based the computer-simulated patient loads, and/or perform other operations for individual units 14. Moreover, a patient load simulation may serve as a basis for further systematic analysis of the patient flow within a facility, which provides the potential for improvement in operational efficiency and cost in the facility.

The description and illustration herein (FIG. 1) of a single unit 14 in a single health care facility 12 is not intended to be limiting. Health care facility 12 may represent any number of health care facilities and unit 14 may represent any number of units within any number of health care facilities 12. The operations performed by system 10 are applied individually to any number of units 14 in any number of facilities 12. The operations performed by system 10 may be simultaneous for different units 14 and/or performed at different times. For example, system 10 may receive past patient census information for a plurality of units 14 (e.g., from the same health care facility 12 and/or from different health care facilities 12) and carry out the operations described herein for the plurality of units at the same time. In some embodiments, health care facilities 12 include health care management systems, hospitals, hospital systems, doctor's offices, collections of doctor's offices, out-patient clinics, and/or other health care facilities. Units 14 may include departments within care management systems and/or hospitals (e.g., an emergency department, an imaging department, a laboratory, a surgical department, a maternity department, a pediatric department, etc.), different types of doctor's offices (e.g., family practitioners, pediatricians, orthopedic doctors, cardiologists, oncologists, geriatric doctors, and/or doctor's with other medical specialties), and/or other units. In some embodiments, system 10 may be used to solve general healthcare labor optimization problems, and/or serve as an analysis tool for analyzing patient flow within a facility 12. In some embodiments, system 10 may be used in non-medical applications such as in airline scheduling, in restaurants, and/or in other applications where customer visit patterns change.

In some embodiments, system 10 comprises one or more computing devices 18, one or more processors 20, electronic storage 22, external resources 24, and/or other components.

Computing devices 18 are configured to provide an interface between users and system 10. In some embodiments, computing devices 18 are associated with health care facility 12, unit 14, and/or other entities; individual caregivers and/or other users associated with health care facility 12 and/or unit 14; service providers (e.g., consultants) to health care facility 12 and/or unit 14; and/or other users and/or entities. Computing devices 18 are configured to provide information to and/or receive information from such users and/or entities. Computing devices 18 include a user interface and/or other components. The user interface may be and/or include a graphical user interface configured to present views and/or fields configured to receive entry and/or selection of patient census information, present information related to unit classifications of units such as unit 14 and/or other units, present computer simulations of patient loads, and/or provide and/or receive other information. In some embodiments, the user interface includes a plurality of separate interfaces associated with a plurality of computing devices 18, processors 20, and/or other components of system 10, for example.

In some embodiments, one or more computing devices 18 are configured to provide a user interface, processing capabilities, databases, and/or electronic storage to system 10. As such, computing devices 18 may include processors 20, electronic storage 22, external resources 24, and/or other components of system 10. In some embodiments, computing devices 18 are connected to a network (e.g., the internet). In some embodiments, computing devices 18 do not include processor 20, electronic storage 22, external resources 24, and/or other components of system 10, but instead communicate with these components via the network. The connection to the network may be wireless or wired. For example, processor 20 may be located in a remote server and may wirelessly receive the patient census information from health care facility 12 and/or unit 14, and/or cause display of the computer-simulated patient loads via the user interface on a computing device 18 associated with health care facility 12 and/or unit 14. In some embodiments, computing devices 18 are laptops, desktop computers, smartphones, tablet computers, and/or other computing devices.

Examples of interface devices suitable for inclusion in the user interface include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that computing devices 18 include a removable storage interface. In this example, information may be loaded into computing devices 18 from removable storage (e.g., a smart card, a flash drive, a removable disk) that enables users to customize the implementation of computing devices 18. Other exemplary input devices and techniques adapted for use with computing devices 18 and/or the user interface include, but are not limited to, an RS-232 port, RF link, an IR link, a modem (telephone, cable, etc.) and/or other devices.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., a server), or processor 20 may represent processing functionality of a plurality of devices operating in coordination (e.g., one or more servers, computing devices 18, devices that are part of external resources 24, electronic storage 22, and/or other devices.)

In some embodiments, processor 20, external resources 24, computing devices 18, electronic storage 22, systems that are part of health care facility 12 and/or unit 14, and/or other components may be operatively linked via one or more electronic communication links. For example, such electronic communication links may be established, at least in part, via a network such as the Internet, and/or other networks. It will be appreciated that this is not intended to be limiting, and that the scope of this disclosure includes embodiments in which these components may be operatively linked via some other communication media. In some embodiments, processor 20 is configured to communicate with external resources 24, computing devices 18, electronic storage 22, the systems that are part of health care facility 12 and/or unit 14, and/or other components according to a client/server architecture, a peer-to-peer architecture, and/or other architectures.

As shown in FIG. 1, processor 20 is configured via machine-readable instructions to execute one or more computer program components. The one or more computer program components may comprise one or more of a census information component 30, a pre-processing component 32, a classification component 34, a simulation component 36, a staffing level component 38, and/or other components. Processor 20 may be configured to execute components 30, 32, 34, 36, and/or 38 by software; hardware; firmware; some combination of software, hardware, and/or firmware; and/or other mechanisms for configuring processing capabilities on processor 20.

It should be appreciated that although components 30, 32, 34, 36, and 38 are illustrated in FIG. 1 as being co-located within a single processing unit, in embodiments in which processor 20 comprises multiple processing units, one or more of components 30, 32, 34, 36, and/or 38 may be located remotely from the other components. The description of the functionality provided by the different components 30, 32, 34, 36, and/or 38 described below is for illustrative purposes, and is not intended to be limiting, as any of components 30, 32, 34, 36, and/or 38 may provide more or less functionality than is described. For example, one or more of components 30, 32, 34, 36, and/or 38 may be eliminated, and some or all of its functionality may be provided by other components 30, 32, 34, 36, and/or 38. As another example, processor 20 may be configured to execute one or more additional components that may perform some or all of the functionality attributed below to one of components 30, 32, 34, 36, and/or 38.

Census information component 30 is configured to obtain past patient census information for an individual unit of a health care facility. The past patient census information comprises a quantity of patient visits to unit 14 during past periods of time. In some embodiments, the quantity of visits to unit 14 comprises an hourly (and/or other time-based metric) quantity of patient visits to unit 14. In some embodiments, the periods of time are weeks of time and/or other epochs of time. In some embodiments, the past patient census information is obtained from servers and/or other databases associated with health care facility 12 and/or unit 14, servers and/or databases included in external resources 24, electronic storage 22, and/or from other sources. In some embodiments, the past patient census information is a part of information typically recorded via computing devices 18 and/or other electronic systems associated with unit 14 and/or health care facility 12. In some embodiments, census information component 30 is configured to obtain week by week past patient census information going back in time for a period of years (e.g., two years or more). For example, unit 14 may electronically record when a patient visits unit 14 for an appointment and/or for other reasons (e.g., an emergency) via a computing device 18 operated by a staff member of unit 14. The past patient census information may include recordings of a series of such visits over time (minutes, hours, days, weeks, months, years) by any number of individual patients to unit 14.

Pre-processing component 32 is configured to pre-process the past patient census information obtained by census information component 30. Pre-processing component 32 is configured to impute missing information and remove outliers from the obtained past patient census information, remove data for holidays and/or holiday weeks from the obtained past patient census information, conduct a change-point analysis that selects the latest ten weeks (and/or any other number and/or time period that allows system 10 to function as described herein) of past patient census information for analysis by classification component 34 and/or simulation component 36, and/or performs other data pre-processing operations.

The imputation of missing information and removal of outliers from the obtained past patient census information may be performed with standard imputation algorithms and/or outlier detection procedures, and/or other techniques. Information for holidays and/or holiday weeks is removed from the obtained past patient census information because holidays create turbulences in patient census patterns and/or for other reasons. For example, a Monday holiday, such as Labor Day and/or Memorial Day in the U.S.A., may effectively push Monday patient visits to unit 14 to Tuesday. A Thursday holiday, such as Thanksgiving in the U.S.A., pushes patient visits to both Wednesday or the following Monday.

The change-point analysis is performed because there may be idiosyncratic trends present in different units 14, potentially together with sudden capacity changes due to organizational and/or physician personnel changes (for example), and/or for other reasons. After a change-point analysis based on weekly (for example) aggregated patient census information that segments a years-long sequence of obtained information into stable segments, pre-processing component 32 selects the latest stable ten (for example) week (for example) long sequence. In some embodiments, stable may refer to no and/or few substantive changes in mean and/or variance of patient loads. For example if the latest stable segment is shorter than ten weeks, but the second-to-last stable segment is longer than ten weeks, then the last ten weeks of the second-to-last stable segment are selected for subsequent analysis (e.g., by classification component 34 and/or simulation component 36). In some embodiments, pre-processing component 32 is configured such that a user may manually select (e.g., via a computing device 18) a period of time (e.g., ten weeks or some other period) as the basis for classification and/or simulation (e.g., as described below) in addition to and/or instead of the automatic selection as described above.

Classification component 34 is configured to determine intra-period and inter-period variation in the quantity of patient visits to unit 14 during the past periods of time. Classification component 34 is configured to determine the intra-period and inter-period variations based on the pre-processed (e.g., by pre-processing component 32) past patient census information. In some embodiments, classification component 34 is configured such that the intra-period variation is intra-week (but this is not intended to be limiting) variation, which is the standard deviation of the number of patient visits to unit 14 within a week averaged over a total number of weeks. In some embodiments, classification component 34 is configured such that the inter-period variation is inter-week (again this is not intended to be limiting) variation, which is the standard deviation of the number of patient visits to unit 14 at a particular hour (a particular hour is used as an example, but this may also be a particular minute, day, etc.) of the week averaged over a total number of hours. Classification component 34 is configured such that both metrics are normalized by dividing by the average number (e.g., per hour) of patient visits to unit 14.

Figure 2:
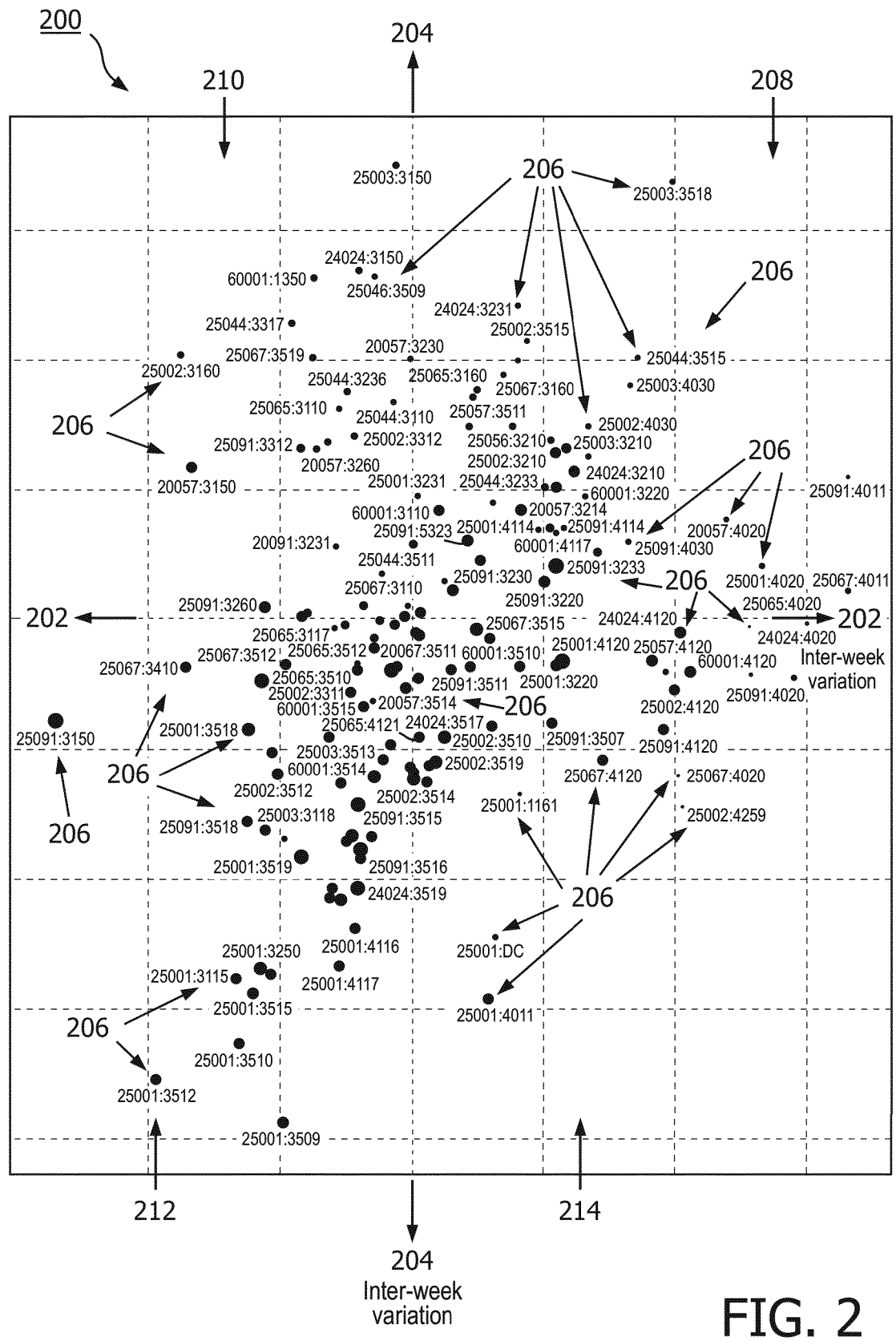
FIG. 2 illustrates a scatter plot showing intra-week variation and inter-week variation for a plurality of units of health care facilities, in accordance with one or more embodiments.

By way of a non-limiting example, FIG. 2 illustrates a scatter plot 200 showing intra-week variation 202 (X-axis) and inter-week variation 204 (Y-axis) for a plurality of units 206 (e.g., similar to units 14 shown in FIG. 1). The quadrants 208 (high intra, high inter), 210 (low intra, high inter), 212 (low intra, low inter), 214 (high intra, low inter) in FIG. 2 correspond to the unit classification categories described below. In FIG. 2, the size of a unit 206 point corresponds to the average volume of patients who visit the unit.

Returning to FIG. 1, classification component 34 is configured to classify individual unit 14 based on the intra-period variation and the inter-period variation. In some embodiments, individual unit 14 is classified into one of two or more categories (e.g., that correspond to simulation algorithms described herein). In some embodiments, the individual unit is classified into at least one of four or more categories (e.g., based on the intra-period and inter-period variations). In some embodiments, the categories comprise predictable-variable, flat-stable, shifting-stable, mixed-variable, and/or other categories.

Predictable-variable is indicative of high intra-week (for example) variation and low inter-week (for example) variation relative to variation in other categories. For example, most emergency departments (e.g., units 14) may fall into this category. Emergency departments may have frequent patient admissions and/or discharges, but the admissions and/or discharges are consistent and occur at similar hours week after week. This is likely because emergency events are by nature random and the intensity of emergency events often follows the periodic daily flow of the community at large.

Flat-stable is indicative of low intra-week (for example) variation and low inter-week (for example) variation relative to variation in other categories. For units 14 categorized in the flat-stable category, within a given week (and/or other period of time), the number of patient visits may stay constant for several hours, and then exhibit a random walk style jump (e.g., up or down), reflecting less frequent patient admission/discharge/transfer (ADT) activities.

Shifting-stable is indicative of low intra-week (for example) variation and high inter-week (for example) variation relative to variation in other categories. Shifting-stable units may be similar to flat-stable units except that the shifting-stable units may have high inter-week variations. Underlying patient volumes may be around a first number one week (and/or over other periods of time), but hover near half or less (or double or more, etc.) of that number some other week. As one possible example, the clinical explanation for this type of variability may be that a physician leaves due to personal matters and/or academic conferences, and/or seasonal changes, and/or returns from such absences.

Mixed variable is indicative of high intra-week (for example) variation and high inter-week (for example) variation relative to variation in other categories. Often, pediatric departments (e.g., units 14) fall into this category. This is likely due to the fact that pediatric care may be individualized and to an extent subject to seasonal factors.

Figure 3:
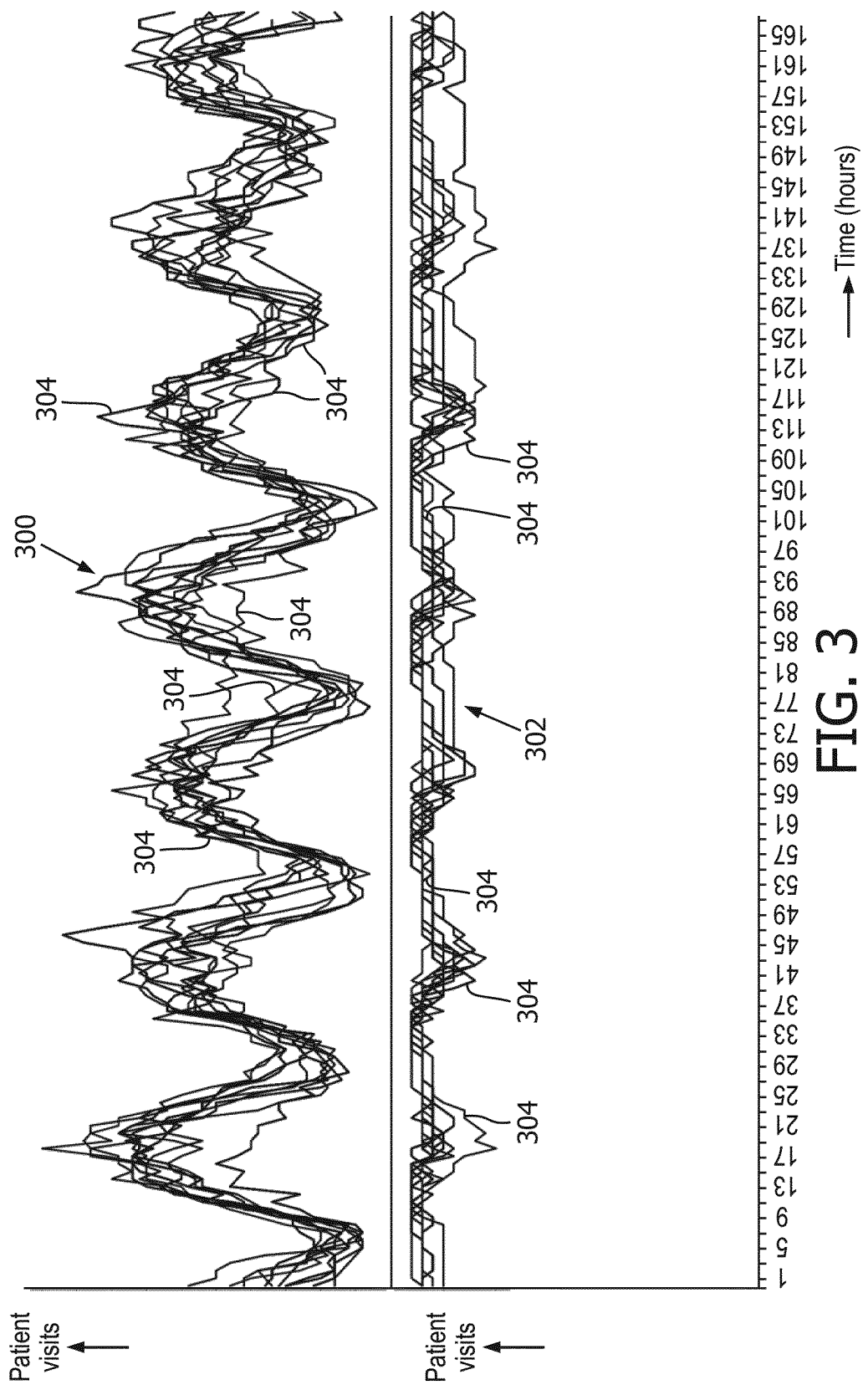
FIG. 3 illustrates patient visit patterns for predictable-variable and for flat-stable unit classifications, in accordance with one or more embodiments.
Figure 4:
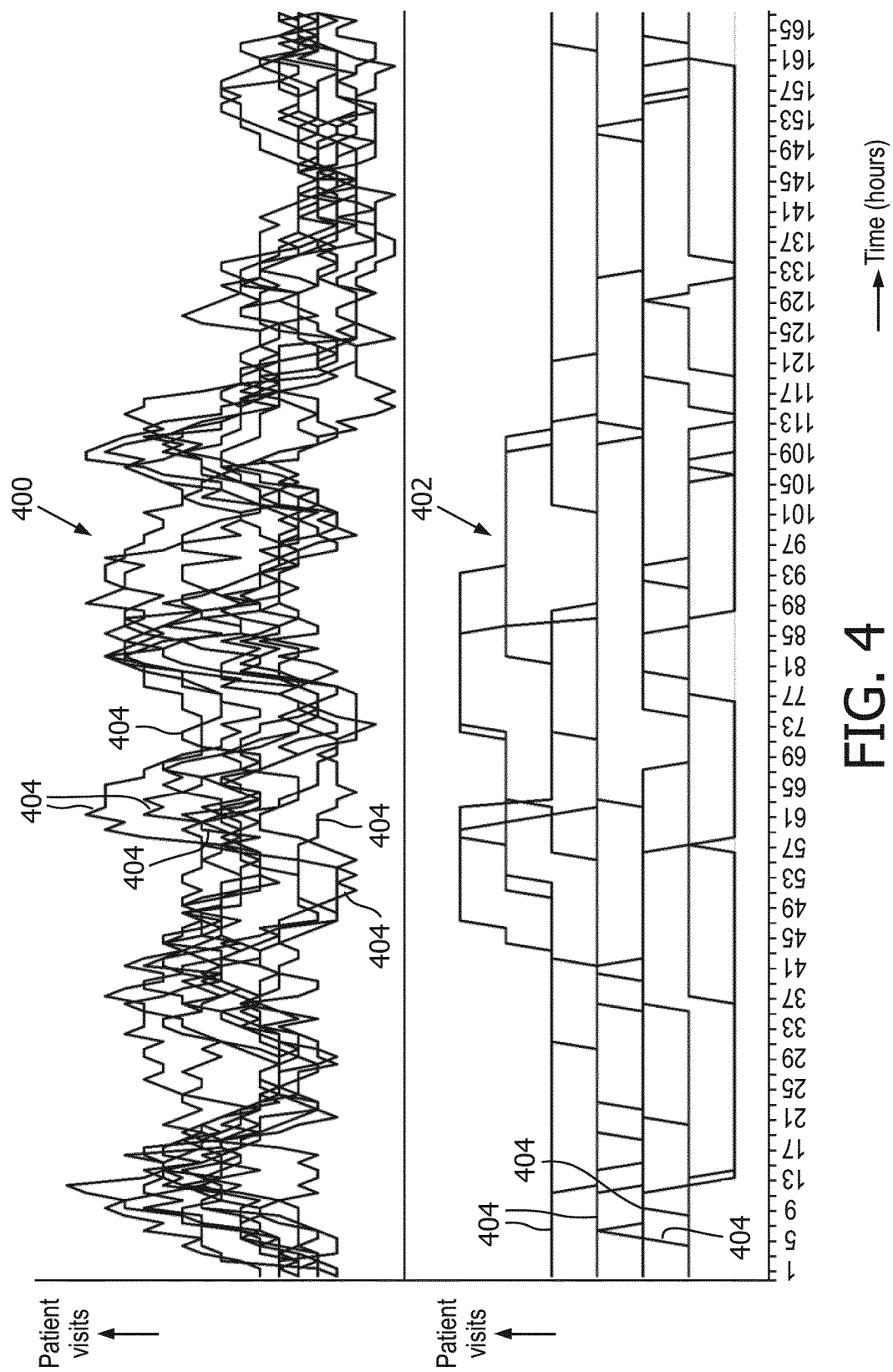
FIG. 4 illustrates patient visit patterns for mixed-variable and for shifting-stable unit classifications, in accordance with one or more embodiments.

Example patient visit patterns for predictable-variable, flat-stable, shifting-stable, and mixed-variable are illustrated in FIG. 3 and FIG. 4. FIG. 3 illustrates patient visit patterns 300 for predictable-variable and 302 for flat-stable. FIG. 4 illustrates patient visit patterns 400 for mixed-variable and 402 for shifting-stable. FIG. 3 and FIG. 4 illustrate weekly patient visit profiles 304, 404 for a plurality of units (e.g., unit 14 shown in FIG. 1) with several weeks of patient visit profiles for several units overlaid. In FIG. 3, patient visit patterns 300 were recorded for an emergency department (unit) of a health care facility. Patient visit patterns 302 were recorded for a unit with few admissions and discharges. In FIG. 4, patient visit patterns 400 were recorded for a unit having large fluctuations in a given week, and large fluctuations in patient visits week to week. Patient visits 402 were recorded for a unit with fewer within-week changes, but relatively (to the other pattern classifications shown in FIG. 3 and FIG. 4) large week to week changes.

Returning to FIG. 1, simulation component 36 is configured to generate a computer simulation of patient loads for an individual unit 14. The computer simulation is generated based on the classification and/or other information. The computer-simulated patient loads comprise a quantity of patient visits (e.g., an hourly quantity) to the individual unit 14 during one or more periods (e.g., future weeks or other periods) of time. The computer simulation is performed using a non-parametric simulation algorithm. In some embodiments, a first non-parametric simulation algorithm is used to simulate the patient loads for the individual unit 14 responsive to the classification being predictable-variable. In some embodiments, a second non-parametric simulation algorithm is used to simulate the patient loads for the individual unit 14 responsive to the classification being flat-stable, shifting-stable, or mixed-variable. In some embodiments, the first simulation algorithm comprises a sequential turning point sampling algorithm and the second simulation algorithm comprises a conditional random walk sampling algorithm.

The sequential turning point sampling algorithm is configured such that a turning point is the hour (and/or other time point) at which a trend in the number of visits conveyed by the patient census information turns, from increasing to decreasing or from decreasing to increasing. Salient features of these trends include the consistent locations (e.g., a particular hour of a week) and values (e.g., hourly patient visit number) at the turning points. The sequential turning point sampling algorithm exploits these features. For example, based on ten weeks of information extracted by pre-processing component 32, the sequential turning point algorithm causes simulation component 36 to determine the turning points (with their locations and values) from the extracted information, and then randomly select turning points from the ten weeks sequentially along 168 hours (of a week) until the last hour is reached. An individual sample includes a sequence of turning points that is a composition from the ten weeks. The sequential turning point algorithm then causes simulation component 36 to apply a local regression smoothing over the turning points and find the patient visit quantity at whole hours. This algorithm produces samples that retain salient features of the predictable variable classification pattern and also reflect uncertainty.

The conditional random walk sampling algorithm targets a stable-jump-stable-jump type succession present in patient visits in the flat stable pattern, the shifting stable pattern, and/or the mixed variable pattern. The conditional random walk sampling algorithm mimics this behavior by randomly starting from a given week (and/or some other time point) and proceeding according a jump table conditional on the hours (and/or some other time point) of a day (for example) constructed from historical data. This conditional jump table is used since patient admission and/or discharge are not uniform throughout a day (for example), and are dependent on the hours of the day. For example, some units 14 may have rules that only allow discharging patients on Monday and Wednesday at 1:00 PM. However, random walks often drift, which means that after a period of time the path of the random walk will tend to diverge significantly from the starting point. Simulation component 36 is configured such that a correction is applied to anchor the simulation to the actual patient census information at midnight points (and/or other time points) for individual days. The resulting samples are then identical at individual midnight points to a randomly selected week (for example), but the path between midnight points will be different from the historical data and from each other, thus reflecting uncertainty.

In some embodiments, simulation component 36 is configured to generate a computer simulation of patient loads for an individual unit 14 describing for past and/or current periods (e.g., weeks or other periods). Simulation component 36 is configured to generate such simulations as described above (e.g., based on the pre-processed and categorized patient census information). Simulation component 36 may be configured to generate computer simulations of patient loads for past and/or current periods to test the accuracy of the simulation (e.g., the simulation may be compared to obtained data) and/or for other reasons.

Staffing level component 38 is configured to recommend one or more staffing levels for an individual unit 14. Staffing level component 38 is configured to recommend one or more staffing levels for an individual unit 14 based on the computer-simulated patient loads. In some embodiments, staffing level component 38 is configured to use various strategies such as mixed integer programming, greedy algorithm, genetic algorithm, simulated annealing, and/or other strategies to generate efficient staff shift allocations and/or assignments.

Figure 5:
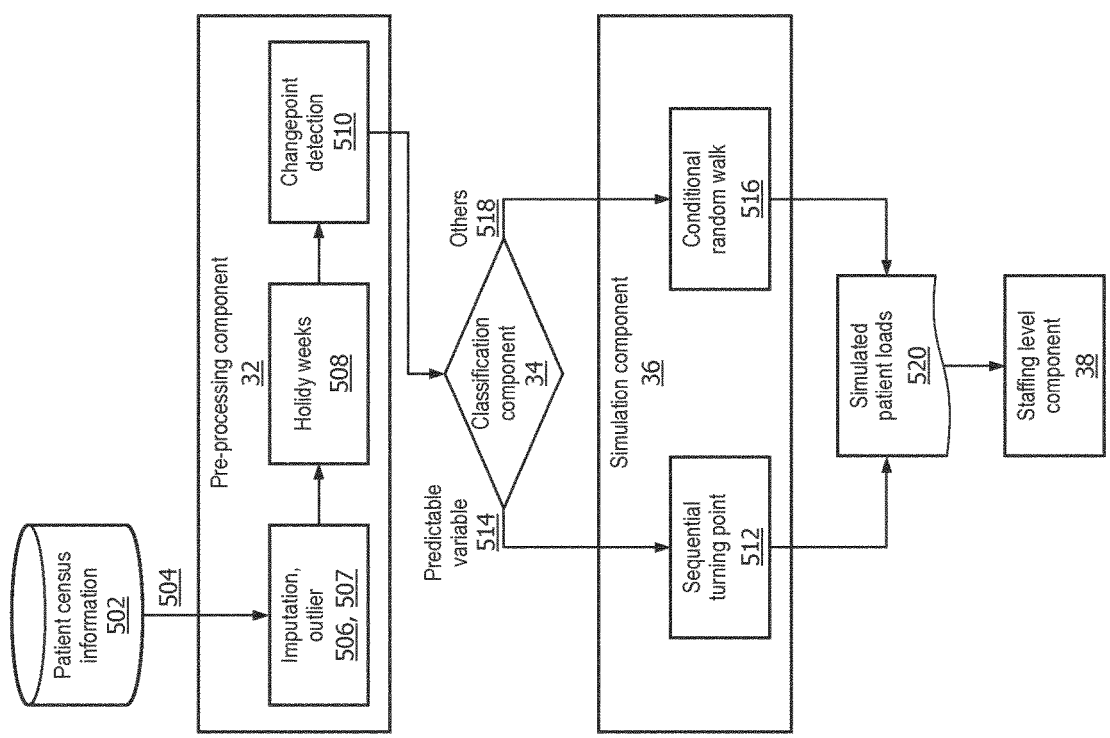
FIG. 5 illustrates example operations performed by a system configured to generate computer simulations of patient loads for units of health care facilities, in accordance with one or more embodiments.

FIG. 5 illustrates example operations performed by system 10 (FIG. 1), in accordance with one or more embodiments. As shown in FIG. 5, patient census information 502 is obtained (e.g., by census information component 30 shown in FIG. 1) and communicated 504 to pre-processing component 32. Pre-processing component 32 imputes 506 missing information and removes 507 outliers from obtained past patient census information 502, removes 508 data for holidays and/or holiday weeks from obtained past patient census information 502, and conducts 510 a change-point analysis of past patient census information 502. Classification component 34 classifies the individual units (e.g., unit 14 shown in FIG. 1) based on intra-period variation and inter-period variation in patient visit patterns. An individual unit is classified into at least one of four categories including predictable-variable, flat-stable, shifting-stable, and mixed-variable. Simulation component 36 is configured to generate a computer simulation 520 of patient loads for an individual unit (e.g., unit 14). The computer simulation is generated based on the classification and/or other information. A sequential turning point 512 non-parametric simulation algorithm is used to simulate the patient loads for the individual unit responsive to the classification being predictable-variable 514. A conditional random walk 516 non-parametric simulation algorithm is used to simulate the patient loads for the individual unit responsive to the classification being flat-stable, shifting-stable, or mixed-variable (others 518). Staffing level component 38 is configured to recommend one or more staffing levels for an individual unit based on the computer-simulated patient loads.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, etc.) or a drive (e.g., a disk drive, etc.). Electronic storage 22 may be (in whole or in part) a separate component within system 10, or electronic storage 22 may be provided (in whole or in part) integrally with one or more other components of system 10 (e.g., a computing device 18, processor 20, etc.). In some embodiments, electronic storage 22 may be located in a server together with processor 20, in a server that is part of external resources 24, in computing devices 18, and/or in other locations. Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information obtained and/or determined by processor 20, information received via computing devices 18 and/or other external computing systems, information received from external resources 24, information received from heath care facility 12 and/or unit 14, and/or other information that enables system 10 to function as described herein. By way of a non-limiting example, electronic storage 22 may store the patient census information obtained by census information component 30, the simulation algorithms used by simulation component 36, the computer simulations generated by simulation component 36, and/or other information.

External resources 24 include sources of information (e.g., databases, websites, etc.), external entities participating with system 10 (e.g., a medical records system of a health care facility that stores patient census information), one or more servers outside of system 10, a network (e.g., the internet), electronic storage, equipment related to Wi-Fi technology, equipment related to Bluetooth® technology, data entry devices, and/or other resources. In some implementations, some or all of the functionality attributed herein to external resources 24 may be provided by resources included in system 10. External resources 24 may be configured to communicate with processor 20, computing device 18, electronic storage 22, health care facility 12 and/or unit 14, and/or other components of system 10 via wired and/or wireless connections, via a network (e.g., a local area network and/or the internet), via cellular technology, via Wi-Fi technology, and/or via other resources.

Figure 6:
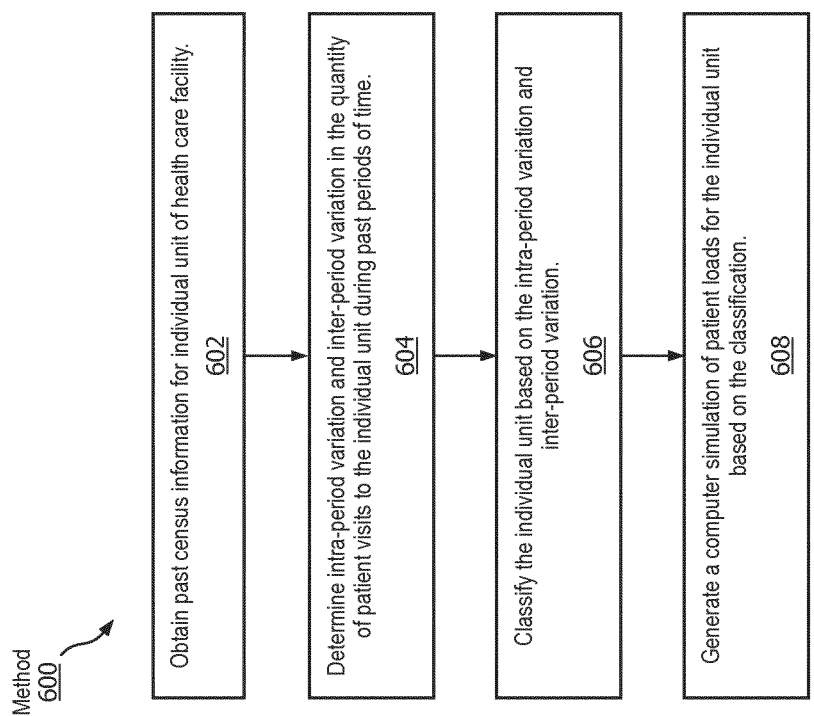
FIG. 6 illustrates a method for generating computer simulations of patient loads for units of health care facilities, in accordance with one or more embodiments.

FIG. 6 illustrates a method 600 for generating computer simulations of patient loads for units of health care facilities, in accordance with one or more embodiments. Method 600 may be performed with a simulation system. The system comprises one or more hardware processors and/or other components. The one or more hardware processors are configured by machine readable instructions to execute computer program components. The computer program components include a census information component, a pre-processing component, a classification component, a simulation component, a staffing level component, and/or other components. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, past patient census information is obtained for an individual unit of a health care facility. The past patient census information comprises a quantity of patient visits to the individual unit during past periods of time. In some embodiments, the quantity of visits to the individual unit comprises an hourly quantity of patient visits to the individual unit. In some embodiments, the periods of time are weeks of time and/or other epochs of time. In some embodiments, operation 602 is performed by a processor component the same as or similar to census information component 30 (shown in FIG. 1 and described herein).

At an operation 604, intra-period and inter-period variation in the quantity of patient visits to the individual unit during the past periods of time is determined. In some embodiments, operation 604 is performed by a processor component the same as or similar to classification component 34 (shown in FIG. 1 and described herein).

At an operation 606, the individual unit is classified based on the intra-period variation and the inter-period variation. In some embodiments, the individual unit is classified into one of two or more categories (e.g., that correspond to simulation algorithms described herein). In some embodiments, the individual unit is classified into at least one of four or more categories (e.g., based on the intra-week and inter-week variation). In some embodiments, the categories comprise predictable-variable, flat-stable, shifting-stable, mixed-variable, and/or other categories. Predictable-variable is indicative of high intra-week variation and low inter-week variation relative to variation in other categories. Flat-stable is indicative of low intra-week variation and low inter-week variation relative to variation in other categories. Shifting-stable is indicative of low intra-week variation and high inter-week variation relative to variation in other categories. Mixed variable is indicative of high intra-week variation and high inter-week variation relative to variation in other categories. In some embodiments, operation 606 is performed by a processor component the same as or similar to classification component 34 (shown in FIG. 1 and described herein).

At an operation 608, a computer simulation of patient loads for the individual unit is generated. The computer simulation is generated based on the classification and/or other information. The computer-simulated patient loads comprise a quantity of patient visits (e.g., an hourly quantity) to the individual unit during one or more periods (e.g., future weeks) of time. The computer simulation is performed using a non-parametric simulation algorithm. In some embodiments, a first non-parametric simulation algorithm is used to simulate the patient loads for the individual unit responsive to the classification being predictable-variable. In some embodiments, a second non-parametric simulation algorithm is used to simulate the patient loads for the individual unit responsive to the classification being flat-stable, shifting-stable, or mixed-variable. In some embodiments, the first simulation algorithm comprises a sequential turning point sampling algorithm and the second simulation algorithm comprises a conditional random walk sampling algorithm. In some embodiments, operation 608 is performed by a processor component the same as or similar to simulation component 36 (shown in FIG. 1 and described herein).

In some embodiments, method 600 further comprises recommending one or more staffing levels for the individual unit based on the computer-simulated patient loads. In some embodiments, this operation is performed by a processor component the same as or similar to staffing level component 38 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system configured to generate computer simulations of patient loads for units of health care facilities, the system comprising one or more hardware processors configured by machine readable instructions to:
   obtain, by one or more computer processors, past patient census information for an individual unit of a health care facility, the past patient census information comprising a quantity of patient visits to the individual unit during past periods of time;
   pre-process the past patient census information, by the one or more computer processors, using a change point analysis to remove effects of idiosyncratic trends specific to the individual unit in the past patient census information,
   determine, by the one or more computer processors, intra-period variation and inter-period variation in the quantity of patient visits to the individual unit during the past periods of time;
   classify, by the one or more computer processors, the individual unit based on the intra-period and inter-period variations;
   generate, by the one or more computer processors, a computer simulation of patient loads for the individual unit based on the classification, the computer-simulated patient loads comprising a quantity of patient visits to the individual unit during one or more future periods of time, the computer simulation performed using a non-parametric simulation algorithm tailored for the individual unit,
      wherein the non-parametric simulation algorithm is tailored for the individual unit by the one or more computer processors by determining and using different non-parametric simulation algorithms for different classifications, such that the classification and the non-parametric simulation algorithm used to generate the computer simulation are specific to the individual unit; and
   determine, by the one or more computer processors, based on the computer simulation of patient loads for the individual unit, optimal staffing levels for the individual unit using mixed integer programming, a greedy algorithm, a genetic algorithm, and/or simulated annealing to tailor the optimal staffing levels for the individual unit.

2. The system of claim 1, wherein the periods of time are weeks of time, and wherein the individual unit is classified into at least one of four categories, the categories comprising:
   predictable-variable, predictable-variable being indicative of high intra-week variation and low inter-week variation relative to variation in other categories;
   flat-stable, flat-stable being indicative of low intra-week variation and low inter-week variation relative to variation in other categories;
   shifting-stable, shifting-stable being indicative of low intra-week variation and high inter-week variation relative to variation in other categories; and
   mixed-variable, mixed variable being indicative of high intra-week variation and high inter-week variation relative to variation in other categories.

3. The system of claim 2, wherein the one or more hardware processors are configured to use a first non-parametric simulation algorithm to simulate the patient loads for the individual unit responsive to the classification being predictable-variable; and use a second non-parametric simulation algorithm to simulate the patient loads for the individual unit responsive to the classification being flat-stable, shifting-stable, or mixed-variable.

4. The system of claim 3, wherein the first simulation algorithm comprises a sequential turning point sampling algorithm and the second simulation algorithm comprises a conditional random walk sampling algorithm.

5. The system of claim 1, wherein the quantity of patient visits to the individual unit comprises an hourly quantity of patient visits to the individual unit.

6. A method for generating computer simulations of patient loads for units of health care facilities with a simulation system, the system comprising one or more hardware processors configured by machine readable instructions, the method comprising:
   obtaining, by one or more computer processors, past patient census information for an individual unit of a health care facility, the past patient census information comprising a quantity of patient visits to the individual unit during past periods of time;

pre-processing the past patient census information, by the one or more computer processors, using a change point analysis to remove effects of idiosyncratic trends specific to the individual unit in the past patient census information;

determining, by the one or more computer processors, intra-period variation and inter-period variation in the quantity of patient visits to the individual unit during the past periods of time;

classifying, by the one or more computer processors, the individual unit based on the intra-period and inter-period variations;

generating, by the one or more computer processors, a computer simulation of patient loads for the individual unit based on the classification, the computer-simulated patient loads comprising a quantity of patient visits to the individual unit during one or more future periods of time, the computer simulation performed using a non-parametric simulation algorithm tailored for the individual unit, wherein the non-parametric simulation algorithm is tailored for the individual unit by the one or more computer processors by determining and using different non-parametric simulation algorithms for different classifications, such that the classification and the non-parametric simulation algorithm used to generate the computer simulation are specific to the individual unit; and determine, by the one or more computer processors, based on the computer simulation of patient loads for the individual unit, optimal staffing levels for the individual unit using mixed integer programming, a greedy algorithm, a genetic algorithm, and/or simulated annealing to tailor the optimal staffing levels for the individual unit.

7. The method of claim 6, wherein the periods of time are weeks of time, and wherein the individual unit is classified into at least one of four categories, the categories comprising:

predictable-variable, predictable-variable being indicative of high intra-week variation and low inter-week variation relative to variation in other categories;

flat-stable, flat-stable being indicative of low intra-week variation and low inter-week variation relative to variation in other categories;

shifting-stable, shifting-stable being indicative of low intra-week variation and high inter-week variation relative to variation in other categories; and mixed-variable, mixed variable being indicative of high intra-week variation and high inter-week variation relative to variation in other categories.

8. The method of claim 7, further comprising using a first non-parametric simulation algorithm to simulate the patient loads for the individual unit responsive to the classification being predictable-variable; and using a second non-parametric simulation algorithm to simulate the patient loads for the individual unit responsive to the classification being flat-stable, shifting-stable, or mixed-variable.

9. The method of claim 8, wherein the first simulation algorithm comprises a sequential turning point sampling algorithm and the second simulation algorithm comprises a conditional random walk sampling algorithm.

10. The method of claim 6, wherein the quantity of patient visits to the individual unit comprises an hourly quantity of patient visits to the individual unit.

11. A system for generating computer simulations of patient loads for units of health care facilities, the system comprising:

one or more computer processors;

one or more computer readable storage devices;

program instructions to obtain past patient census information for an individual unit of a health care facility, the past patient census information comprising a quantity of patient visits to the individual unit during past periods of time;

program instructions to pre-process the past patient census information using a change point analysis to remove effects of idiosyncratic trends specific to the individual unit in the past patient census information;

program instructions to obtain intra-period variation and inter-period variation in the quantity of patient visits to the individual unit during the past periods of time;

program instructions to classify the individual unit based on the intra-period and inter-period variations;

program instructions to generate a computer simulation of patient loads for the individual unit based on the classification, the computer-simulated patient loads comprising a quantity of patient visits to the individual unit during one or more future periods of time, the computer simulation performed using a non-parametric simulation algorithm tailored for the individual unit, wherein the non-parametric simulation algorithm is tailored for the individual unit by the one or more computer processors by determining and using different non-parametric simulation algorithms for different classifications, such that the classification and the non-parametric simulation algorithm used to generate the computer simulation are specific to the individual unit; and program instructions to determine, based on the computer simulation of patient loads for the individual unit, optimal staffing levels for the individual unit using mixed integer programming, a greedy algorithm, a genetic algorithm, and/or simulated annealing to tailor the optimal staffing levels for the individual unit.

12. The system of claim 11, wherein the periods of time are weeks of time, and wherein the individual unit is classified into at least one of four categories, the categories comprising:

predictable-variable, predictable-variable being indicative of high intra-week variation and low inter-week variation relative to variation in other categories;

flat-stable, flat-stable being indicative of low intra-week variation and low inter-week variation relative to variation in other categories;

shifting-stable, shifting-stable being indicative of low intra-week variation and high inter-week variation relative to variation in other categories; and mixed-variable, mixed variable being indicative of high intra-week variation and high inter-week variation relative to variation in other categories.

13. The system of claim 12, wherein a first non-parametric simulation algorithm is used to simulate the patient loads for the individual unit responsive to the classification being predictable-variable; and a second non-parametric simulation algorithm is used to simulate the patient loads for the individual unit responsive to the classification being flat-stable, shifting-stable, or mixed-variable.

14. The system of claim 13, wherein the first simulation algorithm comprises a sequential turning point sampling algorithm and the second simulation algorithm comprises a conditional random walk sampling algorithm.

15. The system of claim 11, wherein the quantity of patient visits to the individual unit comprises an hourly quantity of patient visits to the individual unit.

* * * * *